(12) United States Patent
Gaissmaier et al.

(10) Patent No.: US 9,744,218 B2
(45) Date of Patent: Aug. 29, 2017

(54) MULTI-CHAMBER APPLICATOR FOR GELATIN SOLUTION

(71) Applicant: TETEC TISSUE ENGINEERING TECHNOLOGIES AG, Reutlingen (DE)

(72) Inventors: Christoph Gaissmaier, Kusterdingen-Maehringen (DE); Michael Ahlers, Eberbach (DE)

(73) Assignee: TETEC TISSUE ENGINEERGING TECHNOLOGIES AG, Reutlingen (DE)

( * ) Notice: Subject to any disclaimer, the term of this patent is extended or adjusted under 35 U.S.C. 154(b) by 650 days.

(21) Appl. No.: 14/100,552

(22) Filed: Dec. 9, 2013

(65) Prior Publication Data

US 2014/0170119 A1    Jun. 19, 2014

Related U.S. Application Data

(60) Division of application No. 12/350,330, filed on Jan. 8, 2009, now Pat. No. 8,637,081, and a continuation of application No. PCT/EP2007/006104, filed on Jul. 10, 2007.

(30) Foreign Application Priority Data

Jul. 10, 2006  (DE) ........................ 10 2006 033 168

(51) Int. Cl.
| | |
|---|---|
| *A61K 38/45* | (2006.01) |
| *A61K 47/42* | (2017.01) |
| *A61L 27/22* | (2006.01) |
| *A61K 35/28* | (2015.01) |
| *A61K 35/32* | (2015.01) |
| *A61K 35/12* | (2015.01) |

(52) U.S. Cl.
CPC .............. *A61K 38/45* (2013.01); *A61K 35/28* (2013.01); *A61K 35/32* (2013.01); *A61K 47/42* (2013.01); *A61L 27/222* (2013.01); *A61K 35/12* (2013.01)

(58) Field of Classification Search
CPC .................................................... A61K 38/45
See application file for complete search history.

(56) References Cited

U.S. PATENT DOCUMENTS

| | | | |
|---|---|---|---|
| 5,428,014 | A | 6/1995 | Labroo et al. |
| 5,618,551 | A | 4/1997 | Tardy et al. |
| 5,736,132 | A | 4/1998 | Juergensen et al. |
| 5,834,232 | A | 11/1998 | Bishop et al. |
| 5,936,035 | A | 8/1999 | Rhee et al. |
| 5,939,385 | A | 8/1999 | Labroo et al. |
| 6,007,613 | A | 12/1999 | Izoret |
| 6,730,299 | B1 | 5/2004 | Tayot et al. |
| 2002/0015724 | A1 | 2/2002 | Yang et al. |
| 2002/0198599 | A1* | 12/2002 | Haldimann ............. A61F 2/442 623/17.16 |
| 2003/0095993 | A1 | 5/2003 | Bentz et al. |
| 2005/0002893 | A1 | 1/2005 | Goldmann |
| 2005/0079215 | A1 | 4/2005 | Schleifenbaum et al. |
| 2005/0271719 | A1 | 12/2005 | Wong et al. |
| 2006/0160734 | A1 | 7/2006 | Kusanagi et al. |
| 2006/0171930 | A1 | 8/2006 | Seyda et al. |
| 2007/0077274 | A1 | 4/2007 | Ahlers |
| 2008/0199429 | A1 | 8/2008 | Hollander et al. |
| 2009/0175946 | A1 | 7/2009 | Gaissmaier et al. |

FOREIGN PATENT DOCUMENTS

| | | |
|---|---|---|
| DE | 197 32 917 | 10/1998 |
| DE | 695 17 714 | 11/2000 |
| DE | 694 32 300 | 2/2002 |
| DE | 101 52 407 | 5/2003 |
| DE | 696 30 990 | 12/2004 |
| DE | 600 20 330 | 11/2005 |
| DE | 10 2004 024 635 | 12/2005 |
| EP | 0 856 355 | 8/1998 |
| JP | 2004-283371 | 10/2004 |
| JP | 2005-325075 A | 11/2005 |
| JP | 2006-512944 A | 4/2006 |
| JP | 61-152247 | 7/2006 |
| JP | 2009-542384 A | 12/2009 |
| WO | WO 94/01508 | 1/1994 |
| WO | WO 96/10428 | 4/1996 |
| WO | WO 96/40304 | 12/1996 |
| WO | WO 96/40829 | 12/1996 |
| WO | WO 97/29715 | 8/1997 |
| WO | WO 97/40137 | 10/1997 |
| WO | WO 97/40701 | 11/1997 |
| WO | WO 95/09607 | 4/1998 |
| WO | WO 98/40113 | 9/1998 |
| WO | WO 99/38543 | 8/1999 |
| WO | WO 00/12018 | 3/2000 |
| WO | WO 02/40070 | 5/2002 |
| WO | WO 03/072155 | 9/2003 |
| WO | WO 2005/020849 | 3/2005 |
| WO | WO 2005/111121 | 11/2005 |
| WO | WO 2005/115494 | 12/2005 |
| WO | WO 2005/120464 A1 | 12/2005 |
| WO | WO 2006/014159 A2 | 2/2006 |
| WO | WO 2006/032915 A2 | 3/2006 |
| WO | WO 2006/058215 A2 | 6/2006 |

(Continued)

OTHER PUBLICATIONS

Gelatin Manufacturers Institute of America, Gelatin Handbook, GMIA 2012, p. 1-25.*
McDermott, Martin K., et al., *Biomacromolecules*, 5(4). 1270-1279 (2004).
Chen, Tianhog, et al., *Biomaterials*, 24:2831-2841 (2003).

(Continued)

*Primary Examiner* — Renee Claytor
*Assistant Examiner* — Tiffany Gough
(74) *Attorney, Agent, or Firm* — Leydig, Voit & Mayer

(57) ABSTRACT

Disclosed is a multi-chamber applicator comprising an aqueous gelatin solution and an aqueous cross-linking agent solution in separate chambers.

9 Claims, 6 Drawing Sheets

(56) References Cited

FOREIGN PATENT DOCUMENTS

| WO | WO 2006/059984 | 6/2006 |
| WO | WO 2006/068972 A2 | 6/2006 |
| WO | WO 2006/083384 | 8/2006 |
| WO | WO 2007/057176 | 5/2007 |
| WO | WO 2008/006545 | 1/2008 |

OTHER PUBLICATIONS

Ito, Akira, et al., *Journal of Bioscience and Bioengineering*, 95(2):196-199 (2003).
Broderick, Emmett P., et al., *J Biomet Mater Res B Appl Biomater*, 72:37-42 (2004).
Brown, R. Quin, et al. *J Biomater Res A*, 74:32-38 (2005).
Leubenberger, B.H., *Food Hydrocolloids*, 5(4), 353-361 (1991).

\* cited by examiner

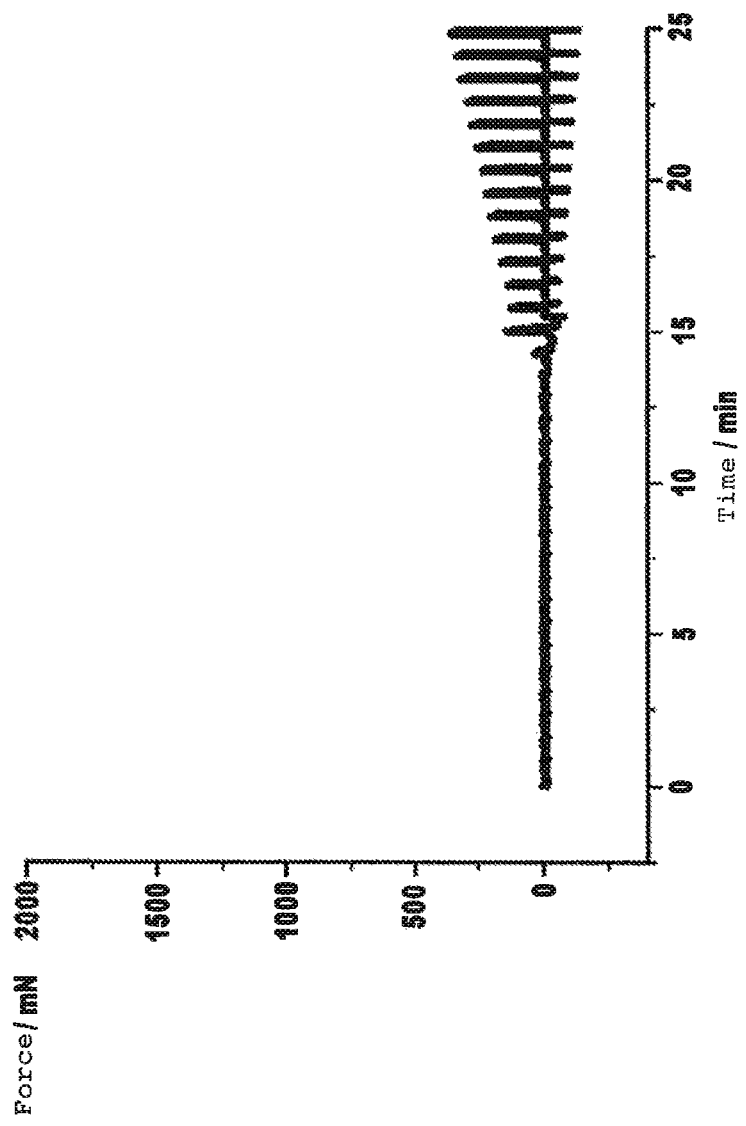

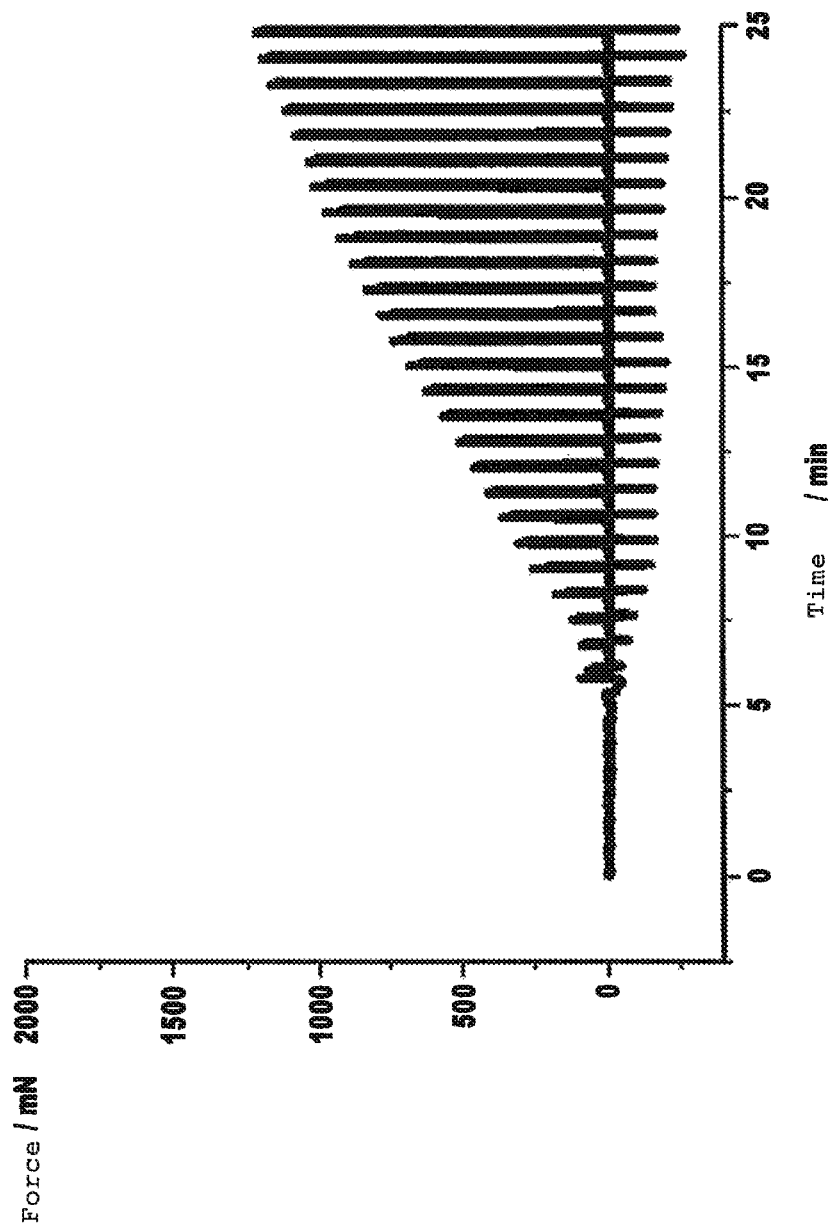

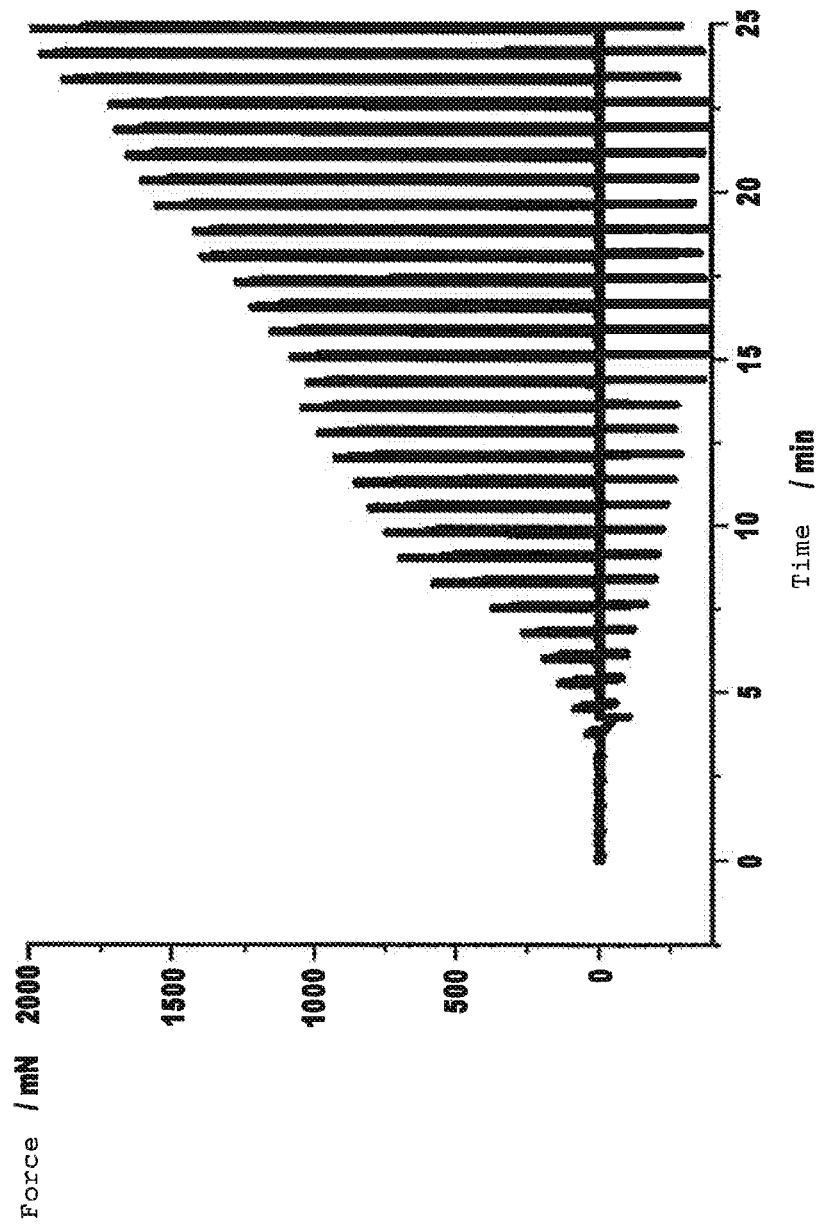

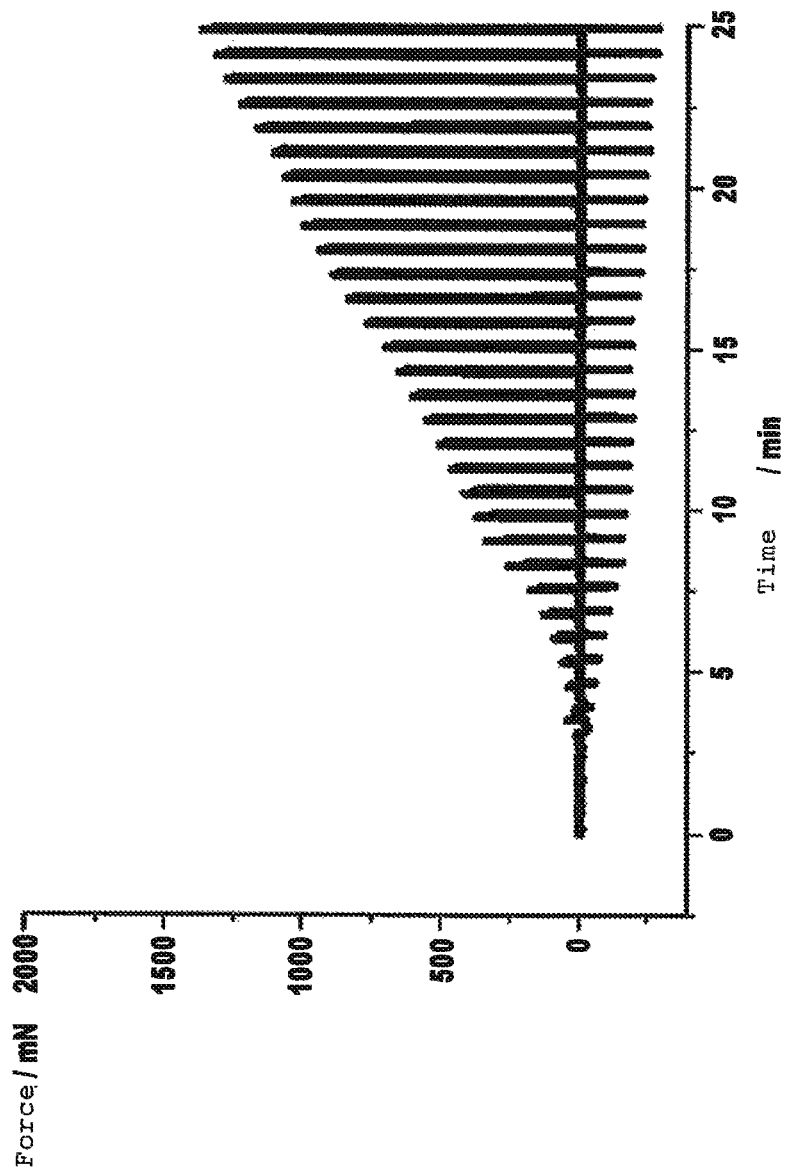

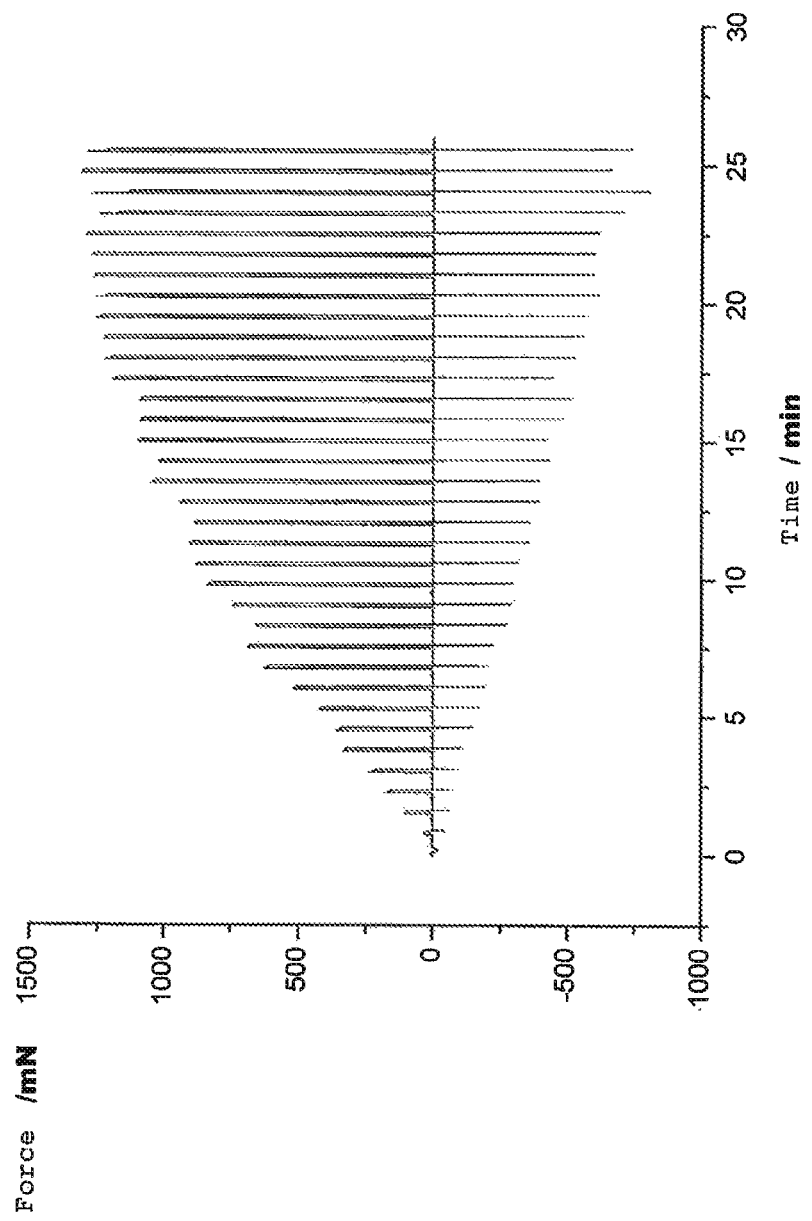

MULTI-CHAMBER APPLICATOR FOR GELATIN SOLUTION

CROSS-REFERENCE TO RELATED APPLICATIONS

This application is a divisional of U.S. patent application Ser. No. 12/350,330, which is a continuation of PCT Application Number PCT/EP2007/006104, filed Jul. 10, 2007, which claims the benefit of German Patent Application Number 10 2006 033 168.0, filed Jul. 10, 2006, which are each incorporated by reference.

BACKGROUND OF THE INVENTION

The invention relates to an innovative use of gelatin and a cross-linking agent for producing a cross-linking therapeutic composition, which forms a cross-linked gelatin gel as a cell matrix in a target area of the human or animal body.

In particular, the invention relates to the use of such a therapeutic composition for treating damage to intervertebral discs, cartilage, menisci, tendons or bone in humans or animals.

Biocompatible, biodegradable matrix materials are used in different fields of medicine. Therapeutic applications, in which the biodegradable material serves as cell matrix, i.e. as a matrix supporting the growth, proliferation and/or differentiation of cells, play an important role therein. These include applications, in which the matrix material is applied or administered cell-free and possibly in conjunction with growth factors in order to perform a growth- or regeneration-promoting function in the target area of the body, as well as applications, in which the matrix material is already colonised by cells in vitro. In the case of the last-mentioned applications, a precultivation of the cells in or on the matrix material can be conducted in vitro, wherein a so-called tissue implant is formed that is then used at the location of the body to be treated. Examples of the described methods are the treatment of bone defects using biomaterials and growth factors (e.g. thrombocyte growth factors or BMPs (bone morphogenetic proteins)) or the treatment of cartilage defects using autologous or allogenic cartilage cell transplantation.

The matrix materials most frequently used for the specified purposes are biopolymers based on proteins or polysaccharides, in particular collagen, gelatin, hyaluronic acid, chitosan or alginates. Preferred forms of application of these materials are gels or sponge structures, which because of their structure allow the cells to be distributed as uniformly as possible. In the case of soluble polymers such as gelatin, for example, these must generally be used in cross-linked form to be able to produce matrices that are dimensionally stable under physiological conditions and have a sufficiently long life. Such shaped bodies based on cross-linked gelatin are described, for example, in the German Patent Application DE 10 2004 024 635 A1.

A further indication, in which a treatment with tissue-specific cells is applicable, is damage to or degeneration of the intervertebral disc, in particular the nucleus pulposus (gelatinous core). A degeneration of the tissue of the nucleus pulposus that can occur with increased likelihood with advancing age leads to higher stress on the annulus fibrosus (fibrous ring), which can ultimately result in it being damaged and thus lead to a prolapsed intervertebral disc.

The intervertebral disc cells of the nucleus pulposus do not have a sufficient capability to regenerate themselves. Therefore, the process of biological intervertebral disc reconstruction is used to prevent the above-described consequences. In this case, intervertebral disc cells or mesenchymal stem cells are cultivated in vitro and then administered to the nucleus pulposus of the patient. A further possibility is to administer suitable growth and differentiation factors to the intervertebral disc using a biomaterial that develop a locally restricted efficacy there and thus contribute to the regeneration of the intervertebral disc. However, it is not possible to implant a solid matrix combined with growth factors or colonised by cells into the nucleus pulposus, since this would inevitably be associated with significant damage to the annulus fibrosus.

For this reason, the cells, the growth factors or a combination of both in a liquid medium, e.g. in a nutrient solution or the like, are injected into the intervertebral disc. However, there is a problem in that the injection path cannot be adequately closed and therefore the cells and/or growth factors suspended in the liquid medium can be pressed out of the intervertebral disc again through the injection path as soon as pressure is exerted on it.

BRIEF SUMMARY OF THE INVENTION

Therefore, a therapeutic composition would be desirable for these and similar biological regeneration methods that can be administered to a target area of the body, wherein it is assured that the suspended cells and/or the growth factors remain in the target area of the body without the patient having to keep the treated body area immobilised for an unreasonably long period.

To solve the specified problems, the use of gelatin and a cross-linking agent is proposed according to the invention for producing a cross-linking therapeutic composition of the aforementioned type which forms a cross-linked gelatin gel as a cell matrix in the target area, wherein i. the gelatin and the cross-linking agent are mixed with one another to form the cross-linking therapeutic composition, which is then administered to the target area; or ii. the gelatin and the cross-linking agent are provided in separate form and are administered simultaneously or consecutively to the target area with the formation of the cross-linking therapeutic composition.

BRIEF DESCRIPTION OF THE SEVERAL VIEWS OF THE DRAWINGS

These and further advantages of the present invention are explained in more detail on the basis of the following examples with reference to the Figures.

FIGS. 1A to 1E: are graphs, in which the gel strength and viscidity of a cross-linked gelatin gel according to the invention are plotted for gelatins with different viscosities in dependence on the reaction time.

DETAILED DESCRIPTION OF THE INVENTION

Figure 2:
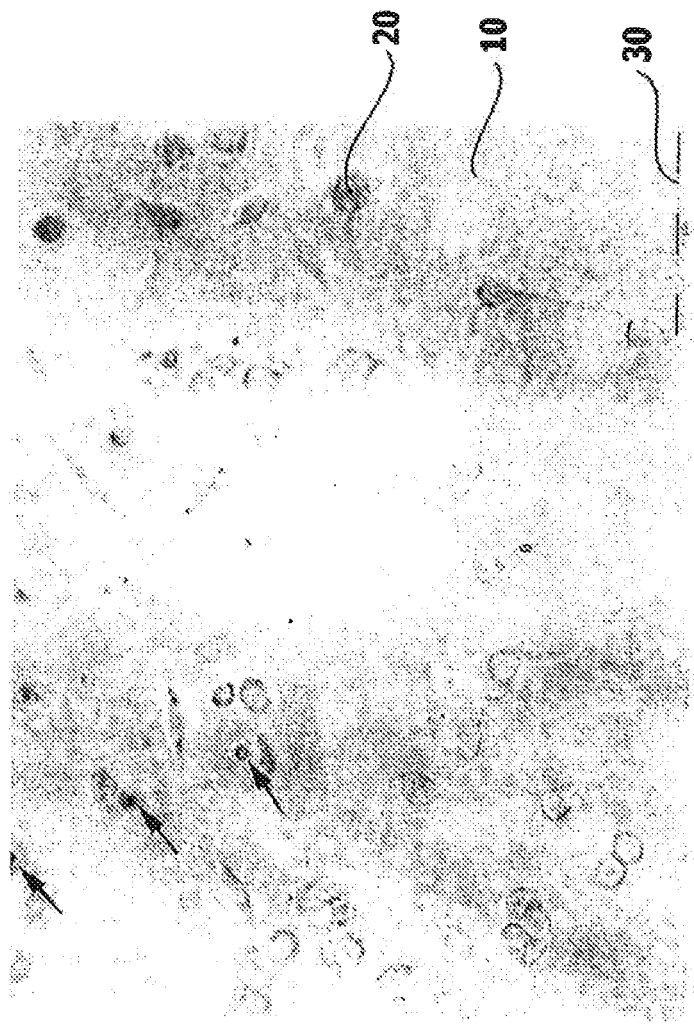
FIG. 2: is a light microscope image of a cross-linked gelatin gel according to the invention with chondrocytes embedded therein.

The idea forming the basis of the invention is to use gelatin, which is distinguished by its water solubility and can therefore be administered in the form of a solution, in particular by injection, as a biodegradable matrix material. The soluble gelatin then changes in the target area into a gelatin gel, which through the action of the cross-linking agent is changed into an insoluble form, i.e. into a cross-linked gelatin gel, which forms a load-bearing cell matrix.

The therapeutic composition according to the invention does not need any further components that contribute to the formation of the cross-linked gelatin gel besides the gelatin and the cross-linking agent. However, this does not exclude the presence of other components that can in some instances provide further advantageous effects.

The cells for which the gelatin gel serves as a matrix can be living cells that are administered to the patient jointly with the therapeutic composition. However, the gelatin gel can also serve as a matrix for ingrowth of the autologous cells located in the target area, wherein the therapeutic composition then preferably comprises growth and/or differentiation factors, which promote the regeneration of these cells or the tissue formed by them.

The above-specified problem is solved by the therapeutic composition according to the invention in that the cross-linked gelatin gel provides a solid matrix that substantially prevents the cells, growth factors or the combination of cells with growth factors from being pressed out of the target area. In addition, the therapeutic composition according to the invention provides the advantage as a result of the formation of a gelatin gel that it allows and stabilises a substantially uniform distribution of active substances and cells in a three-dimensional region contrary to liquid media, in which cells sink as a result of gravity. A further advantage of the cross-linked and then insoluble gelatin is that it binds or fixes the applied growth factors and/or other therapeutic active substances in the target tissue, and thus allows a locally restricted development of the effect in the sense of a controlled and continuous active substance release. Undesirable side-effects that could be caused by cells or active substances discharging again from the intervertebral disc are prevented as a result of this.

The advantages of this cross-linked gelatin gel, i.e. in particular the possibility of embedding cells and/or growth factors three-dimensionally in a solid matrix, can also be utilised in the cultivation of cells in vitro in a similar manner to that in the therapeutic application.

Therefore, the present invention also relates to the use of gelatin and a cross-linking agent for producing a cross-linking composition, which is mixed with cells to be cultivated and which forms a cross-linked gelatin gel as a cell matrix for the in vitro cultivation of the cells in a target area, wherein
  i. the gelatin and the cross-linking agent are mixed with one another to form the cross-linking composition, which is then administered to the target area; or
  ii. the gelatin and the cross-linking agent are provided in separate form and are administered simultaneously or consecutively to the target area with the formation of the cross-linking composition.

In the case of in vitro application, the target area is understood to mean any type of suitable containers, in which a cultivation of cells can be conducted, in particular Petri dishes, culture flasks, shake flasks or the like. The gelatin gel serving as cell matrix can form a layer covering the base of the vessel, for example, or can also completely or partially line the inside wall of the vessel.

The cells to be cultivated and also possibly growth factors are added to the cross-linking composition before any substantial cross-linking occurs. A culture or nutrient solution containing the cells and the dissolved gelatin is preferably prepared that is added to the cross-linking agent before or after being placed in the culture flask, i.e. the target area. In this case, the different methods of provision and administration, which are described in more detail below with a focus on the therapeutic application in vivo, are also used in a corresponding manner in the cultivation of cells in vitro.

Compared to seeding cells onto a solid culture medium, the method according to the invention for cultivating cells in vitro has the advantage that the cells have a three-dimensional matrix available for growth without them having to firstly migrate from the surface into the medium. At the same time, the cells are prevented from settling, which in the case of cultivation in liquid medium can only be achieved by permanently shaking the culture vessel.

Before the different variants of provision and administration of the gelatin and the cross-linking agent are described in detail, the particular advantages that result from the selection of gelatin as matrix material should firstly be outlined.

In contrast to collagen, gelatin is obtainable in a defined and reproducible composition as well as with high purity. In particular, it contains practically no immunogenic telopeptides that could trigger the defence reactions of the body. On this basis, gelatin has an excellent tissue and cell compatibility, which cannot be guaranteed by other resorbable biomaterials such as alginates or chitosan.

While uncross-linked gelatin is soluble at body temperature (37° C.), it can be changed by cross-linking into a gel-like form, i.e. a cross-linked gelatin gel, that is insoluble in these conditions, as already mentioned. Such a gelatin gel can serve as a cell matrix for the growth and differentiation of cells.

At the same time, the cross-linked gelatin gel is completely resorbable, i.e. after a certain period it is broken down without residue in the body. This is a hydrolytic degradation that can be assisted by autologous enzymes, if appropriate.

It is possible, in principle, to use gelatin of different origins within the framework of the present invention, wherein porcine gelatin is preferred, in particular gelatin from pig skin. This is available in a high quality and is already approved for different medical applications.

Besides this, the use of other gelatin types such as fish gelatin, for example, can also provide particular advantages. In particular, the gelatin obtained from cold water fish is distinguished by a relatively low gel point, i.e. aqueous solutions of (uncross-linked) fish gelatin remain liquid at lower temperatures, for example, than solutions of pig skin gelatin of the same concentration. This fact allows dissolved fish gelatin to be provided at room temperature or even cooled, which simplifies handling compared to a provision at elevated temperatures of up to 37° C.

Gelatin types or gelatin materials of different origins and/or different kinds can also be used in a mixture as gelatin according to the invention to adapt the properties of the composition according to the invention even better to the respective application.

To further improve the biocompatibility of the therapeutic composition, it is preferred to use a gelatin with a particularly low content of endotoxins. Endotoxins are metabolites or fragments of microorganisms that occur in raw animal material.

The endotoxin content of gelatin is specified in international units per gram (I.U./g) and determined according to the LAL test, the implementation of which is described in the fourth edition of the European Pharmacopoeia (Ph. Eur. 4).

To keep the content of endotoxins as low as possible, it is advantageous to destroy the microorganisms as early as possible during the course of the gelatin production. Moreover, appropriate hygiene standards should be maintained during the production process.

The endotoxin content of gelatin can thus be drastically reduced by specific measures during the production process. These measures primarily include the use of fresh raw materials (e.g. pig skin) avoiding storage times, with careful cleaning of the entire production plant directly before the start of gelatin production and, if necessary, replacing ion exchangers and filter systems in the production plant.

The gelatin used within the framework of the present invention preferably has an endotoxin content of 1200 I.U./g or less, even more preferred 200 I.U./g or less. Optimally, the endotoxin content lies at 50 I.U./g or less, determined in accordance with the LAL test in each case. In comparison hereto, many commercially available gelatins have endotoxin contents of 20,000 I.U./g and more.

As already mentioned, gelatin that is obtained by extraction from collagen-containing raw materials is a water-soluble product that can be brought into solution in particular at the temperatures suitable for administration, i.e. 37° C. or less. This dissolved form is particularly advantageous for administration in that the gelatin solution can be injected, for example, into the nucleus pulposus of an intervertebral disc or into another damaged tissue such as into cartilage or bone defects, for example. In order to convert the gelatin into a gelatin gel after administration, i.e. in the target area of the body, a cross-linkage of the gelatin occurs according to the invention.

Different types of cross-linking agents are known that convert gelatin by inter- and/or intramolecular linkages into a gelatin gel that is insoluble at temperatures of 37° C. or less. These linkages between the gelatin molecules can concern both covalent bonds and a complex formation, which is based, for example, on ionic interactions, hydrogen bridges or Van der Waals forces.

Modified celluloses, in particular hydroxypropylmethyl cellulose (HPMC), are preferably used as complexing cross-linking agents that cause the gelatin to form a gel by means of non-covalent interactions.

Chemical cross-linking agents, which react with the gelatin forming covalent bonds, can also be used within the framework of the present invention. These preferably relate to multifunctional aldehydes, isocyanates, halides or imides, in particular formaldehyde. However, when selecting the chemical cross-linking agent it should be ensured that this does not have any cytotoxic effects on the body, as is the case, for example, with glutaraldehyde (see e.g. patent document DE 101 52 407 A1). Both the quantity of cross-linking agent to be used and the respective target area in the body should be taken into consideration when assessing possible harmful effects.

Therefore, with the basic requirement of physiological compatibility, application of an enzymatic cross-linking agent is preferred in the present invention. The use of transglutaminase is particularly preferred in this case. This enzyme, which occurs in animals, plants and bacteria, catalyses the hydrolysis of the amide bond of glutamine residues and the cross-linkage of the free acyl group resulting therein with other amino groups. Thus, in the case of proteins, in particular gelatin, transglutaminase primarily catalyses a linkage of glutamine residues with the ε-amino groups of lysine residues, i.e. the formation of both inter- and intramolecular covalent bonds. As a natural enzyme, transglutaminase is recognised as physiologically safe so long as it is used in appropriately purified form.

The use of transglutaminases of bacterial origin that are available in high quality and purity is preferred within the framework of the invention. However, human transglutaminase that can be produced in particular by recombinant gene expression can also be used.

The transglutaminase is preferably used in immobilised form on a support material. This allows a more uniform distribution of the enzyme molecules in the composition, so that a higher activity can be obtained with the same quantity of enzyme. Oligosaccharides are preferred support materials for transglutaminase.

According to the invention, the cross-linkage of the gelatin occurs in the target area of the body, i.e. the gelatin and the cross-linking agent should only come into contact with one another after, during or directly before administration under conditions that allow the cross-linkage reaction to proceed. To ensure that this occurs, different forms of provision and administration of the gelatin and the cross-linking agent are conceivable. The abovementioned fundamental alternatives (i) and (ii) shall be described in more detail below.

According to variant (i) of the invention, the application of the composition occurs so that the gelatin and the cross-linking agent are mixed to form a cross-linking therapeutic composition and this is administered to the target area. Such a composition is preferably an aqueous solution that contains the cross-linking agent and the gelatin in solution.

With this procedure it is ensured that a homogeneous distribution of both components occurs in the solution. Such a solution can also be administered in a simple manner, in particular by simple application to the target area or by injection. However, such a solution should generally only be produced directly before administration in order to prevent the cross-linkage reaction from being too far advanced before reaching the target area and prevent the viscosity of the solution from being too high, for example, for an injection. However, depending on the type of gelatin and the cross-linking agent, it is also possible that a solution containing the two components can be stored for some time, in particular at low temperatures, without the cross-linkage reaction already proceeding to an extent detrimental to administration.

The aqueous solution is preferably produced by dissolving a solid mixture comprising the gelatin and the cross-linking agent preferably in lyophilised form. This form of provision is suitable in particular if transglutaminase is used as cross-linking agent.

The provision of gelatin and cross-linking agent in this solid form, in which the enzymatic reaction cannot proceed, has the advantage that the mixture has a relatively high storage stability. At the same time, handling is simple for the treating doctor, since he/she only needs to dissolve a single solid mixture in a liquid medium that possibly already contains the cells and/or other active substances to be applied.

Dissolution of the solid mixture should take place directly before administration of the aqueous solution, i.e. in particular less than 10 minutes, preferably less than 5 minutes beforehand, based on a predetermined temperature in the respective target area.

Because the gelatin is present in lyophilised form, its dissolution is also significantly improved at lower temperatures. This is important because in many preferred applications of the therapeutic composition cells sensitive to temperatures above 37° C. are administered simultaneously. The dissolution of the solid mixture therefore preferably takes place at a temperature of 37° C. or less. At these temperatures, in particular at room temperature, lyophilised gelatin is readily soluble, since it is present at least predominantly in amorphous form.

With respect to the rate of formation of the gelatin gel and also its strength, the quantity of cross-linking agent used in relation to the quantity of gelatin is of decisive importance. In the case where transglutaminase is used, 0.6 to 80 units of transglutaminase per gram of gelatin, further preferred 5 to 40 units/g, are contained in the above-described mixture. The kinetics of the gel formation resulting from the selection of this ratio, amongst other factors, will be discussed in detail below.

Therefore, with respect to the first variant (i), the present invention also relates to a solid mixture that comprises gelatin and transglutaminase preferably in lyophilised form.

In the case of the abovementioned variant (ii) of the invention, application of the composition occurs so that the gelatin and the cross-linking agent are provided in separate form and are applied simultaneously or consecutively to form the cross-linking therapeutic composition. In this case, the mixing of the two components can occur at different times, as is described below.

A preferred form of provision is that both the gelatin and the cross-linking agent are provided in the form of separate aqueous solutions. These can then be mixed by the treating doctor and administered in the form of a single solution, as has already been described above. In this case, mixing should occur less than 10 minutes, preferably less than 5 minutes, before administration.

However, to more reliably exclude the possibility of the cross-linkage reaction starting too early, it is preferred if the gelatin solution and the cross-linking agent solution come into contact with one another only during or after administration and not before. This can be achieved in particular by a simultaneous application of the two (separate) solutions.

Depending on the type of means used to administer the solutions (e.g. one or more injection cannulas or other applicators), the mixing of the simultaneously applied solutions can occur before, during or after the target area is reached in this case. However, it is advantageous to conduct the mixing as early as possible, i.e. before the target area is reached, in order to assure a high homogeneity of the solution arriving at the target area and thus assure the formation of a uniformly cross-linked gelatin gel.

In a preferred embodiment of the invention, a simultaneous administration of the gelatin solution and the cross-linking agent solution is conducted by injecting both solutions using a multi-chamber applicator, e.g. a dual-chamber syringe. In this case, the gelatin solution and cross-linking agent solution are located in separate chambers of the applicator and are administrated already mixed, for example, by a common injection cannula to the desired target area, e.g. the nucleus pulposus. Therefore, mixing of the two solutions occurs during administration, e.g. upon entry in the cannula. To achieve as intensive a mixing as possible, it is preferred if the multi-chamber applicator comprises a mixing element. In particular, this can be a geometric structure (static mixer) in the flow path of the cannula, at which thorough mixing, in particular swirling, of the two solutions occurs.

Hence, with respect to the second variant (ii), the present invention also relates to a multi-chamber applicator, which contains an aqueous gelatin solution and an aqueous cross-linking agent solution in separate chambers.

Alternatively, it is also possible to administer the aqueous gelatin solution and the aqueous cross-linking agent solution to the target area one after the other and mix them there. It is also assured in this case that the cross-linkage of the gelatin only takes place in the target area.

In a further preferred embodiment of the invention, an aqueous gelatin solution is provided as well as a cross-linking agent in solid form. This variant is particularly suitable in the case of enzymatic cross-linking agents such as transglutaminase, the keeping quality of which is generally higher in this form than in solution. The enzyme can be provided in particular in the form of a lyophilised powder, which is then added in metered dosages to the gelatin solution before administration and then dissolved.

In many preferred applications of the therapeutic composition according to the invention, which will be explained in more detail below, an application of living cells occurs at the same time, wherein these are preferably contained in the aqueous gelatin solution. Because of the temperature sensitivity of these cells, it is preferred that the administration of the aqueous gelatin solution occurs at a temperature of 37° C. or less. However, the production of the gelatin solution can also take place at higher temperatures, e.g. at 60° C., wherein the cells are then only added after cooling to 37° C. or less. If the solution is then stored at room temperature or with cooling, the gelatin can indeed gelate and solidify, but can then be brought back into solution again directly before administration by heating to 37° C.

The concentration of the administered gelatin solution is preferably selected so that the gelatin concentration in the composition amounts to 5 to 20% by wt. It has been found that lower gelatin concentrations generally do not result in gelatin gels with an adequate strength that are readily cross-linked, whereas concentrations of more than 20% by wt. can be unfavourable to the viability of the cells in some instances.

In the case where transglutaminase is used as cross-linking agent, the quantity and concentration thereof in a transglutaminase solution is preferably selected so that, as has already been described in association with variant (i), a quantity of 0.6 to 80 units of transglutaminase per gram of gelatin results in the composition. A ratio of 5 to 40 units/g is further preferred. In this case, the volume of transglutaminase solution selected can generally be significantly lower than that of the gelatin solution, so that the latter is not significantly diluted by mixing with the transglutaminase solution.

The speed of the cross-linkage reaction as well as the strength of the gelatin gel formed are largely dependent on the gelatin concentration in the composition and on the ratio between gelatin and cross-linking agent. These parameters can be varied within the abovementioned preferred ranges to balance the effect of further factors.

Such factors are, for example, the type of gelatin used, in particular its viscosity and average molecular weight, and also the type of cross-linking agent, in particular its type and origin in the case of transglutaminase.

The kinetics and extent of the cross-linkage reaction can be described by means of different physical parameters. To measure these, the formation of the gelatin gel as it proceeds in vivo in the case of a therapeutic application is pursued by a corresponding reaction in vitro. In this case, the start of the cross-linkage reaction is respectively defined by the time at which the gelatin and the cross-linking agent come into contact with one another in the aqueous solution.

The rate of formation of the cross-linked gelatin gel can be characterised in particular by specification of the so-called gel point. In this case, the gel point is defined as the point in time after the start of the cross-linkage reaction at which the storage modulus $G'$ and the loss modulus $G''$ of the gelatin gel are equal in size (see also T. Metzger, Das Rheologie-Handbuch [The manual of rheology], Verlag Vincentz, 2000, pages 173 et seq.).

In an uncross-linked liquid gelatin solution, G' lies clearly below G". During the course of the cross-linkage reaction, i.e. with increasing gelation, both the storage and the loss modulus increase, wherein G' increases more strongly than G". The abovementioned gel point can therefore be determined from the intersection of the two curves in a graph, in which G' and G" are plotted in relation to time. The gel point can also be determined experimentally as the time at which a gel strength (see below) can be measured for the first time during the course of the cross-linkage reaction.

For the use according to the present invention, it is preferred if the gel point of the cross-linked gelatin gel is reached 5 to 180 minutes after the start of the cross-linkage reaction, particularly preferred 10 to 60 minutes and most preferred up to 25 minutes after the start of the cross-linkage reaction. The abovementioned preferred time details are understood to be relative to a predetermined temperature in the respective target area. In the case of a quicker gel formation, there is the risk of the therapeutic composition losing its flowability too early, which in particular can result in the treating doctor not having sufficient time available for administration or in the gel formation advancing too far before the composition has been uniformly distributed in the respective target area. Too slow a gel formation, i.e. a gel point that is too late, in turn has the disadvantage that the respective body part of the patient, e.g. the spinal column in the case of regeneration of an intervertebral disc, must be immobilised for an unreasonably long period.

With respect to the mechanical properties of the cross-linked gelatin gel, it is preferred if this has a gel strength of 100 g or more, measured with a plunger with a diameter of 12.7 mm at a penetration depth of 4 mm. These details relate to pressing a circular plunger with a diameter of 12.7 mm into the gelatin gel perpendicularly to its surface, wherein the plunger is made of polymethyl methacrylate and has a polished surface (see "Standardised Methods for the Testing of Edible Gelatine", Gelatine Monograph, June 2005, GME). In the case of a gel strength of 100 g, the force corresponding to this weight, i.e. 0.981 N, is necessary to press the plunger 4 mm deep into the gelatin gel.

It has already been mentioned that the viscosity of the gelatin used also has an influence on the gel formation besides other factors, wherein a higher viscosity is generally associated with a quicker gel formation. In this context, the viscosity of gelatin is understood to be the viscosity of a 6.7% by wt. standard solution of gelatin in water at 60° C. The viscosity of the gelatin used within the framework of the present invention preferably amounts to 7 mPa·s or more.

The viscosity of gelatin is dependent on its origin as well as on the respective production process, and can be further influenced by specific measures.

In a preferred embodiment of the invention, a gelatin is used that has previously undergone a thermal pretreatment at reduced pressure. As a result of such a pretreatment the viscosity of the gelatin can be increased, wherein this effect is primarily attributable to a thermal elimination of water within the gelatin molecules.

The thermal pretreatment is preferably conducted at temperatures of 80 to 160° C., since below 80° C. the observed effects are relatively little pronounced and above 160° C. an undesirable coloration of the gelatin can occur. Values in the range of 90 to 120° C. are most preferred.

The gel formation is additionally dependent on the molecular weight of the gelatin. The use of gelatin with a high average molecular weight, in particular of 140 kDa or more, is preferred, since in this case an insoluble gelatin gel is already obtained with a lower number of cross-linkage points than in the case of a gelatin with a lower molecular weight.

Alternatively or additionally to a purposeful selection or modification of the gelatin used, the properties of the therapeutic composition according to the invention can also be influenced by mixing together two or more gelatins with different viscosities and/or Bloom values. For example, the rate of gel formation can be varied over a broad range as a result of different mixture ratios of high-viscosity bone gelatin with a low-viscosity fish gelatin.

In a further preferred embodiment of the invention, a partially cross-linked gelatin is used for the production of the therapeutic composition, i.e. the gelatin has already undergone a first (partial) cross-linkage step before the administration according to the invention. As described above, the partially cross-linked gelatin can be administered in mixture with the cross-linking agent or simultaneously or consecutively with this, wherein the formation of the cross-linked gelatin gel in the target area then constitutes a second cross-linkage step.

By using partially cross-linked gelatin, the viscosity of the gelatin solution to be administered can be significantly increased, which is associated with the abovementioned advantages. Moreover, a substantially quicker gel formation can also be achieved by this measure, wherein gel points can be achieved in significantly less than 5 minutes, in particular in the range of a few seconds. A very quick gel formation that occurs almost directly after administration of the therapeutic composition can be advantageous in certain applications.

To ensure that the solution of the partially cross-linked gelatin is highly viscous, but still remains flowable in the conditions of application, the degree of the partial cross-linkage should not be too high. This can be controlled by the conditions in which the partially cross-linked gelatin is produced, in particular by the gelatin concentration, the quantity of cross-linking agent and the duration of the partial cross-linkage reaction. The gelatin used is preferably partially cross-linked by using transglutaminase. Besides the advantages already mentioned above, the use of transglutaminase provides the possibility of stopping the partial cross-linkage reaction by deactivating the enzyme after a defined reaction time, in particular by a thermal denaturing or an oxidising agent such as hydrogen peroxide, for example.

If the partial cross-linkage of the gelatin is achieved by means of transglutaminase, then significantly lower quantities of transglutaminase in relation to the gelatin can be used for this than is the case with the administration of the cross-linking therapeutic composition. The gelatin is preferably partially cross-linked using less than 10 units of transglutaminase per gram of gelatin, in particular using 1 to 3 units of transglutaminase per gram of gelatin.

As described above, the therapeutic composition according to the invention is intended for the formation of a cross-linked gelatin gel as cell matrix, i.e. as a solid matrix, that assists the growth and/or differentiation of cells.

In preferred embodiments of the invention, the therapeutic composition comprises living cells, growth factors or a combination of cells and growth factors, which in particular are administered to the respective target area of the body for the biological regeneration or reconstruction of tissue. Some of these applications shall be discussed in more detail below.

A preferred embodiment of the invention relates to the use of gelatin and a cross-linking agent for producing a cross-linking therapeutic composition for the regeneration of damaged intervertebral discs.

In this case, intervertebral disc damage is understood to mean any degeneration of or impairment to the natural function of the tissue of the intervertebral disc, but in particular in the region of the nucleus pulposus (gelatinous core) or the annulus fibrosus (protective fibrous ring of the intervertebral disc). With advancing age, depending on other influencing factors, a reduction in vitality of the cells in the gelatinous core and/or in the fibrous ring of intervertebral discs can result, which then results in only a restricted production or no further production at all of an extracellular matrix from these cells. However, this extracellular matrix is of decisive importance for the elasticity and therefore the buffer effect of the intervertebral disc, since it is able to bind large quantities of water. As already mentioned, as a result of this degeneration, a substantial loss of function of the intervertebral disc can occur with chronic pain or a prolapsed intervertebral disc can occur as a result of fraying of or damage to the annulus fibrosus.

In the case of biological intervertebral disc reconstruction an attempt is made to counteract such damage cases by introducing cells and/or growth factors into the different structures of the intervertebral disc in order to synthesise a new extracellular matrix there. The use of gelatin and a cross-linking agent according to the present invention is particularly suitable for this, wherein in this embodiment the target area is the nucleus pulposus and/or the annulus fibrosus of the intervertebral disc.

In this case, according to the invention growth factors and/or cells that have possibly been precultivated in vitro are applied jointly with the gelatin and the cross-linking agent to the target area of the intervertebral disc. After distribution of the initially liquid composition in the different structures of the intervertebral disc, the cross-linked gelatin gel forms within a short period after its administration, i.e. preferably within few minutes. This gel ensures that the cells and/or growth factors are fixed in the intervertebral disc in a uniform distribution, while at the same time it prevents the cells and/or growth factors from being pressed out of the intervertebral disc again to a significant extent because of a pressure exerted on the intervertebral disc, since the cross-linked gelatin adheres and thus closes the layered structures of the annulus fibrosus and the entry point of the injection. Therefore, the patient only has to be immobilised or to rest for a relatively short period, i.e. until the formation of the gelatin gel is substantially complete, which can occur, for example, within 5 to 180 minutes.

The application of the therapeutic composition can be conducted in particular by administration of an aqueous solution that contains the gelatin and the cross-linking agent, or by simultaneous administration of an aqueous gelatin solution and an aqueous cross-linking agent solution and mixing these.

These and further variants of provision and administration have already been described above. In both cases, the administration can be conducted in a minimally invasive manner by injection, wherein a multi-chamber injection device is preferably used to conduct the second variant, as described above.

In this case, the cells and/or growth factors to be applied are preferably contained in the aqueous solution, which contains the gelatin and the cross-linking agent, or in the aqueous gelatin solution.

In the case where the administration of a single solution occurs, the provision of the growth factors and/or the cells can occur in particular in the form of a solution or cell suspension in a suitable liquid medium. In a preferred embodiment of the invention a solid mixture composed of gelatin and transglutaminase in lyophilised form is then dissolved in this solution or cell suspension by the treating doctor. As already described, the gelatin is present in largely amorphous form in this case, so that it is soluble at a temperature of 37° C. or less.

In the second case, the growth factors, the cells or a combination of cells with growth factors can already be made available to the doctor in the aqueous gelatin solution, and ideally already in a multi-chamber applicator that is also filled with the cross-linking agent solution to thus minimise the risk of contamination of the growth factors and/or the cells. If the gelatin gelates during storage or transport, it can be brought into solution again by heating the multi-chamber applicator to a temperature of up to 37° C. directly before administration. In this embodiment, the application of the therapeutic composition is particularly simple, since the treating doctor merely inserts an injection cannula under controlled conditions (e.g. with the assistance of imaging processes) at the desired target area and connects the pre-heated multi-chamber applicator hereto.

The cells used as part of the intervertebral disc reconstruction are preferably intervertebral disc cells. These closely resemble cartilage cells (chondrocytes) and are therefore also referred to as chondrogenetic cells. However, mesenchymal stem cells can also be used as an alternative hereto. These cells can be isolated from bone marrow and have the potential to differentiate in the direction of chondrocytes or intervertebral disc cells.

The used cells can be of autologous origin, i.e. they were taken from the patient him/herself, and also of allogenic origin, i.e. from a donor.

When providing the cells to be administered, the procedure is advantageously such that cells of the respective type are isolated from the tissue and precultivated in vitro. An alternative possibility that can also be used within the framework of the present invention is to administer comminuted tissue containing the desired cells with the therapeutic composition. This method can be conducted very quickly and inexpensively compared to a cultivation of cells in vitro. In particular, a piece of tissue is taken from the patient or a donor by biopsy and comminuted mechanically, i.e. using a sterile scalpel or a mill. The resulting pieces of tissue should be small enough to allow a migration of the living cells from the tissue into the cross-linked gelatin gel, i.e. the cell matrix, after administration, and should preferably be smaller than 1 mm$^3$. A suspension of the tissue fragments is then preferably produced (e.g. 300 to 500 mg of tissue in 1 ml of a physiological buffer solution), which can then be mixed with the aqueous gelatin solution or the solution containing the gelatin and the cross-linking agent.

At the target area, i.e. in the nucleus pulposus and/or annulus fibrosus of the intervertebral disc in the above-described case, the cross-linked gelatin gel forms a matrix supporting the growth and/or differentiation of the cells. The fact that the gelatin gel is degraded or resorbed after a certain period and can therefore be successively replaced by the extracellular matrix synthesised by the cells also plays an important role in this case.

To provide the most optimised conditions possible for the cells it is preferred, as already indicated, if the therapeutic composition comprises growth factors or other substances with a protective and stimulating effect for the cells. As part of the intervertebral disc regeneration, such factors are, for example, factors of the TGF-β super family (transforming growth factor beta), insulin, glucosamines, chrondroitin sulphate, hyaluronic acid and also anti-inflammatory active substances (such as IL-1-receptor antagonists) or antibiotic substances. The survival rate, proliferation and differentiation of the cells as well as the metabolic milieu in the target area are positively influenced by such factors.

In general, with respect to the vitality of the cells used, it should be ensured that the aqueous solution containing them has physiological conditions, i.e. in particular a suitable pH value and ionic strength. For example, known buffer systems such as PBS buffer or Hanks buffer can be used. However, it must be ensured in this case that the osmolarity, i.e. the osmotically active total concentration of the solution, is increased by the dissolved gelatin. To avoid negative effects on the cells, this should be compensated by a reduction in the concentration of other components of the buffer system.

In this context, the present invention also relates to a process for regenerating intervertebral disc damage, wherein the process comprises the administration of gelatin, a cross-linking agent as well as intervertebral disc cells and/or chondrocytes and/or mesenchymal stem cells and/or growth factors to the nucleus pulposus and/or annulus fibrosus of the intervertebral disc separately or already mixed before the target area is reached.

Analogously, as has been described in association with intervertebral disc damage, the therapeutic composition of the present invention can also be applied in the region of the meniscus or articular or non-articular cartilage. On this basis, the invention also relates to the use of gelatin and a cross-linking agent for producing a cross-linking therapeutic composition for regeneration of damaged meniscus or cartilage.

Besides the intervertebral disc, cartilage tissue also has an extremely low intrinsic regeneration ability. Therefore, in the case of damage, e.g. in the case of injury-related cartilage lesions resulting from a trauma, an osteochondrosis dissecans or in the case of limited degenerative cartilage damage, autologous or allogenic chondrocytes are introduced into the defective area to produce new extracellular matrices there (autologous or allogenic cartilage cell transplantation).

Advantageously, the administration of these cells, in particular in the case of spatially smaller defects, can be achieved by application of the therapeutic composition of the present invention, as has already been described in association with intervertebral disc regeneration. The cells used in this case can be chondrocytes and/or mesenchymal stem cells, wherein the latter have the potential to differentiate towards chondrocytes.

A further preferred embodiment of the invention relates to the use of gelatin and a cross-linking agent for producing a cross-linking therapeutic composition for regenerating bone or tendon defects in different anatomical locations of the movement mechanism. With these indications the cross-linking gelatin can also be applied to the defect with growth factors, differentiation factors and/or cells as well as with other regeneration-promoting or also antibiotic substances in a minimally invasive or an open manner (e.g. in combination with bone autografts or allografts, ceramic or other load-bearing materials).

EXAMPLES

Example 1: Cross-Linkage of Gelatin with Transglutaminase: Effect of the Viscosity of the Gelatin As a model system for the medical application of the therapeutic composition according to the invention the cross-linkage of gelatin with the enzymatic cross-linking agent transglutaminase was conducted in vitro and the kinetics of the formation of a cross-linked gelatin gel determined.

Production of a Transglutaminase Stock Solution

A recombinant transglutaminase from human keratinocytes was used for this example and those described below. A stock solution of transglutaminase with a concentration of 30 units/ml was produced by dissolving the corresponding amount of the enzyme in distilled water at room temperature. The solution was sterilised by filtration, frozen in portions of 1.5 ml each using liquid nitrogen and stored at approximately −18° C. Alternatively, the portions can be stored at +4° C.

Thermal Pretreatment of Gelatin at Reduced Pressure

For the cross-linkage with transglutaminase, pig skin gelatins with different viscosities were used in accordance with the following Table 1. The specification of viscosity in this case relates to the viscosity of a 6.7% by wt. aqueous solution of the gelatin at 60° C.

TABLE 1

| Designation | Viscosity (mPa · s) |
|---|---|
| Gelatin A | 3.73 |
| Gelatin B | 5.83 |
| Gelatin C | 7.62 |
| Gelatin D | 8.65 |

The high-viscosity gelatins C and D were respectively produced by a thermal pretreatment of gelatins of lower viscosity. In this case, gelatin C was obtained by thermal pretreatment of gelatin B and gelatin D was obtained by thermal pretreatment of a further pig skin gelatin with a viscosity of 6.41 mPa·s.

The thermal pretreatment of the gelatin at reduced pressure was conducted so that approximately 700 g of gelatin in ground form were respectively held under a vacuum of approximately 14 mbar for 4 hours at 105° C. by means of a rotary evaporator. The gelatin was then allowed to cool overnight in a closed vessel.

Execution of the Cross-Linkage Reaction

For each of the four gelatins A, B, C and D, a 10% by wt. solution of gelatin was produced in a mixture comprising 30% by vol. of PBS buffer (pH 7.2) and 70% by vol. of distilled water. For this, the gelatin was dissolved at 60° C. and the temperature of the resulting homogeneous solution was regulated to 37° C.

All the cross-linkage reactions were conducted at a constant temperature of 37° C. in order to approach as far as possible the conditions prevailing in the therapeutic application. For each batch 5 ml of the 10% by wt. gelatin solution were placed in a cylindrical vessel with a diameter of 3 cm, the temperature of which was regulated to 37° C. by means of an aluminium block. The cross-linkage reaction was started by adding 0.3 ml of the transglutaminase stock solution (30 units/ml) and 0.9 ml of distilled water, each preheated to 37° C., and immediately mixing the resulting reaction mixture thoroughly. This corresponds to an enzyme quantity of 18 units/g relative to the gelatin.

Determination of the Gel Strength as a Function of the Reaction Time

During the course of the cross-linkage reaction, the gel strength and the viscidity of the reaction mixture were determined at intervals of 50 sec by means of a force/distance measuring device of the type Zwick BZ 2.5/TN1S (manufacturer: Zwick GmbH & Co. KG, Ulm).

The determination procedure is such that in each measurement cycle, i.e. every 50 sec, a circular plunger with a diameter of 12.7 mm is plunged or pressed 4 mm deep into the surface of the reaction mixture perpendicularly thereto and the force required for this is measured. The plunger, which has a polished polymethyl methacrylate surface, is then pulled upwards again. If a cross-linked gelatin gel is already present, this adheres to the plunger during its removal. The necessary force to pull the plunger so far upwards that the gelatin gel detaches is also measured.

The measured force as a function of the reaction time (start of the cross-linkage reaction at 0 min.) for the four batches with gelatins A, B, C and D is plotted in FIGS. 1A to 1D. The positive force values indicate the force necessary to press the plunger in, i.e. the gel strength (981 mN correspond to a gel strength of 100 g). The negative force values indicate the viscidity of the gelatin gel, i.e. the force required to remove the plunger until the gelatin gel detaches.

During an initial phase of the reaction, both the gel strength and the viscidity lie substantially at zero, i.e. a flowable solution is present. In the medical application, this corresponds to the period, in which the mixture can be administered to the target area of the body. The earliest time at which a gel strength noticeably different from zero can be measured is the gel point. At this time, the storage modulus G' and the loss modulus G" are the same magnitude.

The different gel points of batches A to D are listed in the following Table 2, wherein the values are respectively averaged from three experiments.

TABLE 2

| Batch | Viscosity | Gel Point | Gel Strength after 10 min |
| --- | --- | --- | --- |
| Gelatin A | 3.73 mPa · s | 14 min | 281 mN/cm² |
| Gelatin B | 5.83 mPa · s | 5 min | 536 mN/cm² |
| Gelatin C | 7.62 mPa · s | 3.3 min | 837 mN/cm² |
| Gelatin D | 8.65 mPa · s | 2.3 min | not determined |

It is evident that the gel point correlates with the viscosity of the gelatin used, i.e. with the same quantity of cross-linking agent gel formation occurs substantially more quickly in a high-viscosity gelatin, than in a low-viscosity one. The gel strength obtained is also dependent on the starting material, as is evident from FIGS. 1A to 1D: after 25 min gel strengths of clearly more than 100 g in some instances were achieved in the case of gelatins B, C and D, whereas in the case of gelatin A with the lowest viscosity only approximately 40 g were reached.

Example 2: Cross-Linkage of Gelatin with Transglutaminase: Effect of the Gelatin Concentration In this example the thermally pretreated gelatin C from Example 1 was cross-linked with different gelatin concentrations with transglutaminase. The preparation of the reaction mixtures and the measurement of the gel strength were conducted as described in Example 1.

The concentration of the gelatin solutions used, the composition of the reaction mixtures and the gel point resulting from the gel strength measurement are shown in the following Table 3.

TABLE 3

| | Batch | | |
| --- | --- | --- | --- |
| | 2-1 | 2-2 | 2-3 |
| Concentration of the gelatin solution | 5% by wt. | 8% by wt. | 10% by wt. |
| Gelatin solution | 5.9 ml | 5.9 ml | 5 ml |
| Transglutaminase stock solution | 0.2 ml | 0.3 ml | 0.3 ml |
| Distilled water | — | — | 0.9 ml |
| Transglutaminase per gram of gelatin | 20.3 units/g | 19.1 units/g | 18.0 units/g |
| Gel point | 5.0 min | 4.0 min | 3.3 min |

The results show that the gel formation can be accelerated by an increase of the gelatin concentration. This trend is clearly evident in the conducted tests, although in the case of the higher gelatin concentrations the quantity of cross-linking agent was slightly lower in relation to the gelatin.

In the medical application of the composition according to the invention, it must be considered in this context that an increase of the gelatin concentration to values beyond approximately 20% by wt. in some circumstances can have negative effects on the viability of cells provided in the gelatin solution.

Example 3: Cross-Linkage of Gelatin with Transglutaminase: Effect of the Quantity of Cross-Linking Agent In this example the thermally pretreated gelatin C from Example 1 was cross-linked with different quantities of transglutaminase.

A 5% by wt. solution of gelatin C was produced as described in Example 1. For each batch, 5.9 ml of this solution were preheated to 37° C. and mixed with the quantity of transglutaminase stock solution (30 units/ml heated to 37° C.) specified in the following Table 4 in order to start the cross-linkage reaction. The determination of the gel point by means of the gel strength measurement occurred as described in Example 1.

TABLE 4

| | Batch | | | |
| --- | --- | --- | --- | --- |
| | 3-1 | 3-2 | 3-3 | 3-4 |
| Quantity of Trans-glutaminase stock solution | 0.1 ml | 0.2 ml | 0.3 ml | 0.5 ml |
| Trans-glutaminase per gram of gelatin | 10.2 units/g | 20.3 units/g | 30.5 units/g | 50.8 units/g |
| Gel point | 14.0 min | 5.0 min | 4.0 mins | 3.0 min |

As can be seen from the values specified in Table 4, the rate of formation of the cross-linked gelatin gel can also be influenced by the concentration of the cross-linking agent, in this case the transglutaminase. As expected, a higher quantity of cross-linking agent leads to a quicker gel formation.

Example 4: Cross-Linkage of Gelatin with Transglutaminase in a Cell Culture Medium In this example gelatin C from Example 1 was cross-linked in different concentrations with different quantities of transglutaminase in a buffer solution particularly well suited to the cultivation of cells. For this, an aqueous gelatin solution was produced in a mixture of 80% by vol. of the cell culture medium DMEM/F12 (Dulbecco's Modified Eagel Medium, BioWhittaker) and 20% by vol. of FB Serum (foetal calf serum, PAA Laboratories). The cross-linkage reaction and the measurement of the gel strength were otherwise conducted as described in Example 1 with the ratios respectively specified in Table 5.

TABLE 5

|  | Batch | | | |
| --- | --- | --- | --- | --- |
|  | 4-1 | 4-2 | 4-3 | 4-4 |
| Gelatin concentration | 12.7% by wt. | 8% by wt. | 8% by wt. | 6% by wt. |
| Quantity of gelatin solution | 5.9 ml | 5.9 ml | 5.9 ml | 5.9 ml |
| Quantity of transglutaminase stock solution | 0.3 ml | 0.3 ml | 0.2 ml | 0.2 ml |
| Transglutaminase per gram of gelatin | 12.0 U/g | 19.1 U/g | 12.7 U/g | 16.9 U/g |
| Transglutaminase concentration | 1.45 U/ml | 1.45 U/ml | 0.98 U/ml | 0.98 U/ml |
| Gelation | 3.0 min | 5.0 min | 8.0 min | 11.0 min |
| Gel strength 10 min after gel point | 1420 mN | 620 mN | 470 mN | 280 mN |

The results show that the cross-linkage of gelatin with transglutaminase can also be conducted without problem in a cell culture medium, which is suitable for the cultivation and application of living cells. As in the preceding examples, it is also evident here that the rate of gel formation and the gel strength obtained can be varied over a broad range by the selection of the gelatin and cross-linking agent concentration.

Example 5: Cross-Linkage of Non-Gelating Gelatin with Transglutaminase

In this example a gelatin that does not gelate under the conditions of the standard Bloom test was used. This gelatin obtained from fish skin is characterised as follows:
Gel strength: 0 g Bloom
Viscosity (6.7% by wt., 60° C.) 2.1 mPa·s
Conductivity: 115 μS
Molecular weight (GPC): 70,840 Da The fish gelatin was mixed in different concentrations with different quantities of transglutaminase in accordance with the procedure described in Example 1. The respective ratios, gel points and gel strengths are evident from the following Table 6.

TABLE 6

|  | Batch | | | |
| --- | --- | --- | --- | --- |
|  | 5-1 | 5-2 | 5-3 | 5-4 |
| Gelatin concentration | 10% by wt. | 5% by wt. | 15% by wt. | 15% by wt. |
| Quantity of gelatin solution | 5.0 ml | 5.9 ml | 5.4 ml | 4.8 ml |

TABLE 6-continued

|  | Batch | | | |
| --- | --- | --- | --- | --- |
|  | 5-1 | 5-2 | 5-3 | 5-4 |
| Quantity of transglutaminase stock solution | 0.3 ml | 0.5 ml | 1.0 ml | 1.6 ml |
| Distilled water | 0.9 ml | — | — | — |
| Transglutaminase per gram of gelatin | 18 U/g | 51 U/g | 37 U/g | 67 U/g |
| Gel point | 60 min | 30 min | 14.5 min | 9.0 min |
| Gel strength 10 min after gel point | (not determined) | 30 mN | 395 mN | 711 mN |

Cross-linked gelatin gels can also be produced using low-viscosity fish gelatin, wherein, as expected, compared to high-viscosity gelatins gel formation occurred very slowly and lower gel strengths were achieved overall. However, as batches 5-3 and 5-4 show, by using both high gelatin concentrations and high quantities of cross-linking agents, values are also readily obtained here that are comparable with the values obtained with high-viscosity gelatins.

A particular advantage in the use of non-gelating fish gelatin is that the gelatin solution remains liquid at room temperature and the provision and handling of the therapeutic composition is simplified as a result.

By using mixtures of different gelatin types, e.g. fish gelatin with cattle bone gelatin or pig skin gelatin, provides a further possibility (besides variation of the gelatin and cross-linking agent concentration) to influence the gel point and the gel strength of the cross-linking therapeutic composition.

Example 6: Cross-Linkage of Gelatin with Transglutaminase: Use of a Partially Cross-Linked Gelatin In this example the gelatin was firstly subjected to a partial (first) cross-linkage step to increase the initial viscosity of the gel solution and to obtain a significantly quicker gel formation in the actual (in this case second) cross-linkage step.

A gelatin made from pig bones with a Bloom value of 250 g and a viscosity of 6.6 mPa·s (6.7% by wt. at 60° C.) serves as starting material for the production of the partially cross-linked gelatin. A 10% by wt. solution of this gelatin in distilled water was prepared by firstly swelling the gelatin for 45 minutes at room temperature and then dissolving it for one hour at 60° C. The temperature of the solution was then regulated to 50° C. and the corresponding quantity of transglutaminase stock solution (30 units/ml) was added, so that a quantity of 1.5 units of transglutaminase per gram of gelatin was present. To conduct the partial cross-linkage the solution was held at 50° C. for 2 hours with agitation.

To stop the cross-linkage reaction, the transglutaminase was thermally deactivated by heating the solution to 80° C., then the solution was cooled immediately in an ice bath, poured into a dish and allowed to gelate. The gelatin gel obtained was minced, dried at 20° C. and at a relative air humidity of 10% and then ground. The partially cross-linked gelatin obtained in this way is referred to below as P2.

A further partially cross-linked gelatin with a slightly higher degree of cross-linkage was produced as described above, except that the partial cross-linkage reaction was conducted for 3 hours. This gelatin is referred to below as P3.

The Bloom values and viscosities at 60° C. and 37° C. of the initial gelatin P0 and the partially cross-linked gelatins P2 and P3 are shown in the following Table 7.

TABLE 7

|  | Gelatin | | |
| --- | --- | --- | --- |
|  | P0 | P2 | P3 |
| Bloom value | 250 g | 228 g | 257 g |
| Viscosity (6.7% by wt., 60° C.) | 6.6 mPa · s | 9.6 mPa · s | 16.7 mPa · s |
| Viscosity (10% by wt., 37° C.) | 28.6 mPa · s | 69.8 mPa · s | 200 mPa · s |

As a result of the partial cross-linkage, the viscosity of the gelatin at 60° C. could be increased approximately 1.5-fold (P2) or approximately 2.5-fold (P3) compared to the uncross-linked gelatin (P0). The effect of the increase in viscosity is even more significant at 37° C., i.e. at a preferred application temperature of the therapeutic composition. Here, the viscosity increased approximately 2.5-fold or approximately 7-fold.

A cross-linkage reaction with transglutaminase was conducted using gelatins P0, P2 and P3 and the gel strength and viscidity were determined as a function of the reaction time, as described in Example 1. In each case, the starting point was 5 ml of a 10% by wt. gelatin solution, to which 1.2 ml of the transglutaminase stock solution (30 units/ml) were added. This corresponds to an enzyme quantity of 72 units per gram of gelatin.

The measurement results are listed in the following Table 8.

TABLE 8

|  | Batch | | |
| --- | --- | --- | --- |
|  | P0 | P2 | P3 |
| Gel point | 1.5 min | 50 sec | <5 sec |
| Gel strength after 10 min | 1184 mN/cm² | 592 mN/cm² | 631 mN/cm² |
| Adhesion after 10 min | 316 mN/cm² | 197 mN/cm² | 237 mN/cm² |

It is evident that the gel point of the cross-linked gelatin gel can be reached substantially more quickly as a result of the partial cross-linkage of the gelatin. Particularly noteworthy is the result achieved with gelatin P3, i.e. an almost immediate gel formation within less than 5 sec after mixing the gelatin with the transglutaminase.

In FIG. 1E the measured force is represented as a function of the reaction time for the batch with gelatin P3 (measurement conducted as described in Example 1). It is clear from the Figure that in spite of the gelation, which occurs almost directly after mixing, the gel strength and the adhesion continuously increase and reach their maximum only some time after gel point. This effect is extremely advantageous for the application of the present invention and as a result the therapeutic composition can be still plastically deformable for a certain period after application and can be adapted to the structure of the target area.

Example 7: Production and Dissolution Behaviour of a Lyophilised Solid Mixture of Gelatin and Transglutaminase This example describes the production of a solid mixture containing 6 units of transglutaminase per gram of gelatin.

75 g of gelatin A from Example 1 (pig skin gelatin with 290 g Bloom) were swelled in 425 g of distilled water and dissolved at 60° C. The solution was allowed to cool to 45° C., mixed with 15 ml of the transglutaminase stock solution (30 U/ml, see Example 1) and thoroughly mixed. Two freeze-drying trays were cooled with liquid nitrogen, the solution containing gelatin and transglutaminase distributed therein and frozen using liquid nitrogen. The frozen solution was lyophilised for two days in a Lyovac GT 2-s freeze-drying installation (manufacturer: AMSCO Finn-Aqua GmbH, Hürth).

The lyophilised solid mixture obtained was ground to a fine powder in a mortar under constant cooling with liquid nitrogen and then dried in a vacuum. Since the powder is highly hygroscopic, it was stored hermetically sealed at approximately 4° C.

A further solid mixture was produced by repeating the described procedure with the same ratios, but by using a cold water-soluble instant gelatin in place of gelatin A. This instant gelatin contains proportions of low-molecular gelatin hydrolysate to improve its solubility.

The dissolution behaviour of the solid mixtures produced in this way was examined as follows: 50 mg of solid mixture in each case were weighed into a sealable tube and mixed with 950 µl of PBS buffer (pH 7.2) preheated to 37° C. The tubes were shaken using a test tube shaker and the time up to visible dissolution of the solid mixture determined.

The mixture produced from gelatin A was dissolved after 2.7 min, the mixture produced from the instant gelatin was dissolved after only 2 min.

The example shows that lyophilised gelatin can be dissolved at 37° C. in an aqueous solution. This is attributable to the fact that the gelatin is present largely in amorphous form as a result of the freeze-drying process. The dissolution rate can be improved even further by using instant gelatin.

Such lyophilised solid mixtures of gelatin and a cross-linking agent can be advantageously used within the framework of the present invention. The mixture can be provided at room temperature or cooled and can then be dissolved at 37° C. or less by the treating doctor in an aqueous solution that possibly contains the cells to be administered.

Example 8: Embedding Porcine Chondrocytes in a Gelatin Gel Cross-Linked with Transglutaminase In this example the vitality of porcine chondrocytes in a cross-linked gelatin gel was examined over a period of several days.

In this case, a gelatin concentration of approximately 17% by wt. and a quantity of 16 units of transglutaminase per gram of gelatin were selected.

A 20% by wt. solution of gelatin A from Example 1 was produced by dissolving the gelatin at 60° C. in a mixture of 35% by vol. of Hanks buffer and 75% by vol. of distilled water. The dilution of the Hanks buffer with water was conducted in the aim of at least partially compensating the osmolarity of the solution increased as a result of the gelatin.

200 µl of the gelatin solution were preheated to 37° C. and mixed with 10 µl of a cell suspension, which contains approximately 10,000 porcine chondrocytes, and also with 21.3 µl of transglutaminase stock solution (30 U/ml). The mixture was pipetted onto a cover plate and incubated for 10 min in the incubator at 37° C., wherein a cross-linked gel containing the cells (cell matrix) was formed. This was covered with a 3 ml layer of cell culture medium and incubated further at 37° C.

The cross-linked gelatin gel (cell matrix) remained stable under these conditions for at least seven days, i.e. it substantially maintained its external shape. This shows that the therapeutic composition according to the present invention can serve as a stable, three-dimensional matrix for the cells embedded therein.

The vitality of the cells was determined by staining the cross-linked gelatin gel with propidium iodite. With this staining dead cells become visible under the fluorescence microscope by a red coloration. In tests after three, five or seven days it was demonstrated that only a very small, substantially constant number of dead cells were present in each case.

FIG. 2 shows a light microscope image of the cell matrix of a cross-linked gelatin gel 10 treated with propidium iodite with the chondrocytes 20 embedded therein after an incubation period of three days. The bar 30 on the lower right edge of the image corresponds to a length of 100 μm. The dead cells that appear red under the fluorescence microscope are marked by arrows. It is clearly evident in the Figure that the predominant proportion of the cells in the gelatin gel is still vital after three days. Similar results were observed after five and seven days.

This result shows that the gelatin gel formed from the composition according to the invention is capable of acting as a matrix assisting the cell growth of mammalian cells.

Example 9: Embedding of Human Chondrocytes in a Gelatin Gel Cross-Linked with Transglutaminase In this example, the effect of the cross-linked gelatin gel on the growth behaviour of human chondrocytes was examined. In this case, different gelatin concentrations were tested with a constant concentration of the cross-linking agent transglutaminase.

For each of the five batches, there were used 250 μl of a solution of gelatin A from Example 1 with the respective concentration according to the following Table 9. The solutions were each inoculated with 250,000 human chondrocytes in a well of a 48-well cell culture plate, mixed with 12.5 μl of transglutaminase stock solution (30 U/ml) at a temperature of 40° C. and incubated at 37° C. for one week. For comparison, no transglutaminase was added to batch 9-4 and buffer was used instead of a gelatin solution in batch 9-5. The results are given in Table 9.

TABLE 9

| | Batch | | | | |
|---|---|---|---|---|---|
| | 9-1 | 9-2 | 9-3 | 9-4 | 9-5 |
| Gelatin concentration | 12.5% by wt. | 4.2% by wt. | 3.0% by wt. | 12.5% by wt. | — |
| Transglutaminase | + | + | + | − | + |
| Transglutaminase per gram of gelatin | 19 U/g | 57 U/g | 80 U/g | — | — |
| Gel point | <1 min | approx. 5 min | <10 min | — | — |
| Result cell colonisation | 3 | 2 | 1 | 2 | 4 |

After cultivation for a week at 37° C. the cells were examined microscopically. As the cell colonisation result, the cell density and the morphology of the cells were assessed and evaluated according to a scale of 1 to 6, wherein 1 stands for a very good cell compatibility and 6 for a cell incompatibility of the cross-linked gelatin gel.

The best result was obtained with a gelatin concentration of 3.0% by wt. (batch 9-3). The cells were rounded, small and had scarcely any vacuole formation. An increase of concentration to 4.3 or 12.5% by wt. (batches 9-2 and 9-1) had a tendency to result in a decrease in cell density in the matrix and to an enlargement of the vacuoles. The uncross-linked gelatin solution used in the comparative test (batch 9-4) was likewise not recognisably harmful to the chondrocytes, but resulted in a marked fibroblast-like morphology. The presence of transglutaminase without gelatin (batch 9-5) resulted in a substantial vacuole formation of the cells.

This test shows that favourable growth and survival conditions for human cells can be achieved by a suitable choice of the gelatin concentration.

The invention claimed is:

1. A multi-chamber applicator, comprising an aqueous gelatin solution and an aqueous cross-linking agent solution in separate chambers, wherein the gelatin is a partially cross-linked gelatin, wherein the aqueous gelatin solution and/or the cross-linking agent solution contain anti-inflammatory and/or antibiotic substances, wherein the cross-linking agent comprises transglutaminase, wherein the aqueous gelatin solution and/or the cross-linking agent solution contain living cells, wherein the living cells comprise intervertebral disc cells, chondrocytes, and/or mesenchymal stem cells, and wherein the gelatin has an endotoxin content of 1200 I.U./g or less.

2. A multi-chamber applicator, comprising an aqueous gelatin solution and an aqueous cross-linking agent solution in separate chambers, wherein the gelatin is a partially cross-linked gelatin, wherein the aqueous gelatin solution and/or the cross-linking agent solution contain anti-inflammatory and/or antibiotic substances, wherein the aqueous gelatin solution and/or the cross-linking agent solution contain living cells, wherein the living cells comprise intervertebral disc cells, chondrocytes, and/or mesenchymal stem cells, and wherein the gelatin has an endotoxin content of 1200 I.U./g or less.

3. The applicator according to claim 1, wherein the gelatin is porcine gelatin.

4. The applicator according to claim 1, wherein the gelatin has a viscosity, which amounts to 7 mPa·s or more.

5. A multi-chamber applicator, comprising an aqueous gelatin solution and an aqueous cross-linking agent solution in separate chambers, wherein the gelatin is a partially cross-linked gelatin, wherein the aqueous gelatin solution and/or the cross-linking agent solution contain anti-inflammatory and/or antibiotic substances, wherein the gelatin has previously undergone a thermal pretreatment at reduced pressure, wherein the aqueous gelatin solution and/or the cross-linking agent solution contain living cells, wherein the living cells comprise intervertebral disc cells, chondrocytes, and/or mesenchymal stem cells, and wherein the gelatin has an endotoxin content of 1200 I.U./g or less.

6. The applicator according to claim 5, wherein the thermal pretreatment is conducted at temperatures of 80 to 160° C.

7. The applicator according to claim 1, wherein the gelatin is partially cross-linked by using transglutaminase.

8. The applicator according to claim 1, wherein the gelatin is partially cross-linked using less than 10 units of transglutaminase per gram of gelatin.

9. The applicator according to claim 1, wherein the aqueous gelatin solution and/or the cross-linking agent solution contain growth and/or differentiation factors.

* * * * *